(12) United States Patent
Schmelzer et al.

(10) Patent No.: US 8,357,352 B2
(45) Date of Patent: Jan. 22, 2013

(54) AEROSOL SUSPENSION FORMULATIONS CONTAINING TG 227 EA OR TG 134 A AS PROPELLANT

(75) Inventors: Christel Schmelzer, Ingelheim (DE); Arne Froemder, Ingelheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 637 days.

(21) Appl. No.: 11/169,876

(22) Filed: Jun. 29, 2005

(65) Prior Publication Data

US 2006/0002863 A1 Jan. 5, 2006

(30) Foreign Application Priority Data

Jul. 2, 2004 (DE) .......................... 10 2004 032 322
May 17, 2005 (DE) .......................... 10 2005 023 334

(51) Int. Cl.
*A61K 9/12* (2006.01)
(52) U.S. Cl. ........................................... 424/45; 424/46
(58) Field of Classification Search .................. 514/826, 514/851, 291, 312; 424/45, 46, 400, 43
See application file for complete search history.

(56) References Cited

U.S. PATENT DOCUMENTS

| | | | |
|---|---|---|---|
| 5,225,183 A | 7/1993 | Purewal et al. | |
| 5,676,930 A | 10/1997 | Jager et al. | |
| 5,682,875 A | 11/1997 | Blower et al. | |
| 5,836,299 A | 11/1998 | Kwon | |
| 5,919,435 A | 7/1999 | Taylor et al. | |
| 5,955,058 A | 9/1999 | Jager et al. | |
| 6,036,942 A | 3/2000 | Alband | |
| 6,045,778 A * | 4/2000 | Jager et al. | 424/45 |
| 6,092,696 A | 7/2000 | Thomas | |
| 6,234,362 B1 | 5/2001 | Thomas | |
| 6,261,539 B1 | 7/2001 | Adjei et al. | |
| 6,305,371 B1 | 10/2001 | Frid et al. | |
| 6,306,368 B1 | 10/2001 | Taylor et al. | |
| 6,423,298 B2 | 7/2002 | McNamara et al. | |
| 6,475,467 B1 | 11/2002 | Keller et al. | |
| 6,511,652 B1 | 1/2003 | Ashurst et al. | |
| 6,739,333 B1 | 5/2004 | Hoelz et al. | |
| 6,983,743 B2 * | 1/2006 | Hoelz et al. | 128/200.23 |
| 7,566,803 B2 | 7/2009 | Lu | |
| 7,776,315 B2 | 8/2010 | Pairet et al. | |
| 7,914,770 B2 | 3/2011 | DeStefano et al. | |
| 2001/0031244 A1 | 10/2001 | Lewis et al. | |
| 2002/0076382 A1* | 6/2002 | Kaplan et al. | 424/43 |
| 2002/0122826 A1 | 9/2002 | Lizio et al. | |
| 2003/0066525 A1 | 4/2003 | Lewis et al. | |
| 2003/0089368 A1 | 5/2003 | Zhao | |
| 2003/0089369 A1 | 5/2003 | Lewis et al. | |
| 2003/0190287 A1 | 10/2003 | Lewis et al. | |
| 2003/0206870 A1 | 11/2003 | Lewis et al. | |
| 2004/0184994 A1 | 9/2004 | DeStefano et al. | |
| 2005/0118107 A1 | 6/2005 | Burns et al. | |
| 2005/0129621 A1 | 6/2005 | Davies et al. | |
| 2005/0152846 A1 | 7/2005 | Davies et al. | |
| 2006/0002863 A1 | 1/2006 | Schmelzer et al. | |
| 2007/0183982 A1 | 8/2007 | Berkel et al. | |
| 2009/0092559 A1 | 4/2009 | Hoelz et al. | |
| 2011/0014134 A1 | 1/2011 | Weil et al. | |

FOREIGN PATENT DOCUMENTS

| | | |
|---|---|---|
| DE | 102004032322 A1 | 2/2006 |
| EP | 0 990 437 A1 | 4/2000 |
| EP | 1219293 A2 | 7/2002 |
| EP | 1241113 A1 | 9/2002 |
| EP | 1 527 772 A1 | 5/2005 |
| WO | 93/15741 A1 | 8/1993 |
| WO | WO 93/15741 * | 8/1993 |
| WO | WO-93/15741 * | 8/1993 |
| WO | 9413262 A1 | 6/1994 |
| WO | 9502651 A1 | 1/1995 |
| WO | 9701611 A1 | 1/1997 |
| WO | 9856349 A1 | 12/1998 |
| WO | 9905464 A1 | 12/1999 |
| WO | 0030607 A1 | 6/2000 |
| WO | 0030608 A1 | 6/2000 |
| WO | WO 00/33892 | 6/2000 |
| WO | 02/05785 A1 | 1/2002 |
| WO | 0217882 A1 | 3/2002 |
| WO | 03002169 A2 | 1/2003 |
| WO | 2004/084858 A2 | 10/2004 |
| WO | 2006002840 A2 | 1/2006 |
| WO | 2006064283 A1 | 6/2006 |
| WO | 2007118802 A1 | 10/2007 |

OTHER PUBLICATIONS

Neale et al., "Medicaments", Aug. 19, 1993, International Application Published Under the PCT, WO 93/15741. (Previously submitted).*
Wiens et al. "Chest Pain in Otherwise Healthy Children and Adolescents is Frequently Caused by Exercise Induced Asthma" Sep. 1, 1992, Pediatrics, vol. 90 No. 3, abstract.*
International Search Report for PCT/EP2005/006865 mailed Sep. 18, 2006.
Robert O. Williams, et al; Influence of Metering Chamber volume and Water Level on the Emitted dose of a Suspension-Based pMDI Containing Propellant 134a; Pharmaceutical Research (1997) vol. 14, No. 4 pp. 438-443.

* cited by examiner

*Primary Examiner* — Ali Soroush
(74) *Attorney, Agent, or Firm* — Michael P. Morris; Anthony P. Bottino

(57) ABSTRACT

Disclosed are propellant gas formulations containing at least one suspended active substance which contains chemically bound water, water and the propellant TG 227 or TG 134 a.

9 Claims, No Drawings

AEROSOL SUSPENSION FORMULATIONS CONTAINING TG 227 EA OR TG 134 A AS PROPELLANT

APPLICATION DATA

This application claims benefit to German applications DE 10 2004 032 322.4 filed Jul. 2, 2004 and DE 10 2005 023 334.1 filed May 17, 2005.

FIELD OF THE INVENTION

The invention relates to pressurised gas preparations for metered-dose aerosols wherein a pharmaceutical composition is formulated as a suspension in TG 227 ea (1,1,1,2,3,3,3-heptafluoropropane) or TG 134 a (1,1,1,2-tetrafluoroethane) as propellant, and the use thereof for preparing a pharmaceutical composition. It preferably relates to an inhalable aerosol.

BACKGROUND

Ever since the public discussions on the ozone-damaging potential of certain chlorofluorocarbons there has been intensive work in the field of alternative propellants for pharmaceutical metered-dose aerosols. It has been known since the early 1990s that the propellant gases TG 227 ea or TG 134 a may be used as alternative propellant gases for aerosols.

It has now been found that, surprisingly, propellant gas formulations with suspended particles of active substance and TG 227 ea or TG 134 a as propellant can be stabilised if the propellant gas or propellant gas mixture contains a certain amount of water.

DETAILED DESCRIPTION OF THE INVENTION

For the propellant formulations according to the invention TG 227 ea and/or TG 134 a are used as propellant gases, optionally in admixture with one or more other propellant gases, preferably selected from among propane, butane, pentane, dimethylether, $CHClF_2$, $CH_2F_2$, $CF_3CH_3$, isobutane, isopentane and neopentane.

Preferred suspensions according to the invention are those which contain as propellant gas only TG 227 ea or only TG 134 a.

If a mixture of the propellant gases TG 227 ea and TG 134a is used in the suspension formulations according to the invention, the proportions by weight in which these two propellant gas components may be used may be freely variable, although TG 227 ea must be present.

In mixtures with one or more other propellant gases, selected from among propane, butane, pentane, dimethylether, $CHClF_2$, $CH_2F_2$, $CF_3CH_3$, isobutane, isopentane and neopentane, the proportion of this other propellant gas component is preferably less than 60%, preferably below 40% and most preferably less than 30%.

The active substances used are preferably active substances which incorporate or bind one or more water molecules in their particle structure. The water is not only physically mixed with the particles of active substance. Preferably the particles of active substance are crystals and the water is water of crystallisation or complex-bound water or water which is otherwise chemically bound, e.g. hydrates. This form of water incorporation is hereinafter also referred to as chemically bound water. In these cases the water generally also affects the crystalline structure of the active substance molecule.

Compounds which are effective by inhalation are preferably used, with the result that the suspension formulations according to the invention are preferably intended for inhalation.

Particularly preferred in this context are pharmaceutical compositions selected from among the anticholinergics, betamimetics, steroids, phosphodiesterase IV inhibitors, LTD4-antagonists and EGFR-kinase inhibitors, antiallergics, ergot alkaloid derivatives, triptanes, CGRP antagonists, phosphodiesterase-V inhibitors, and combinations of active substances of this kind, e.g. betamimetics plus anticholinergics or betamimetica plus antiallergics. In the case of combinations at least one of the active substances contains chemically bound water. Anticholinergic-containing active substances are preferably used, as monopreparations or in the form of combined preparations.

The following are specific examples of the active ingredients or the salts thereof:

Anticholinergics to be used are preferably selected from among tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate-methobromide, tropenol 2-fluoro-2,2-diphenylacetate-methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, 2,2-diphenylpropionate cyclopropyltropine methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl cyclopropyltropine 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the solvates and/or hydrates thereof.

Betamimetics which may be used are preferably selected from among albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2

(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of the racemates, enantiomers or diastereomers thereof and optionally in the form of the pharmacologically acceptable acid addition salts, solvates and/or hydrates thereof.

Steroids which may be used are preferably selected from among prednisolone, prednisone, butixocortpropionate, RPR-106541, flunisolide, beclomethasone, triamcinolone, budesonide, fluticasone, mometasone, ciclesonide, rofleponide, St-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate, (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate and etiprednol-dichloroacetate (BNP-166), optionally in the form of the racemates, enantiomers or diastereomers thereof and optionally in the form of the salts and derivatives thereof, the solvates and/or hydrates thereof.

PDE IV inhibitors which may be used are preferably selected from among enprofyllin, theophyllin, roflumilast, ARIFLO (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropyl-methoxybenzamide, NCS-613, pumafentine, (−)-p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropyl-methoxy-4-difluoromethoxyphenyl)cyclohexan-1-ol], (R)-(+)-ethyl [4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, CDP840, Bay-198004, D-4418, PD-168787, t-440, t-2585, arofyllin, atizoram, V-11294A, C1-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers thereof and optionally in the form of the pharmacologically acceptable acid addition salts, solvates and/or hydrates thereof.

LTD4-antagonists which may be used are preferably selected from among montelukast, 1-(((R)-(3-(2-(6,7-difluoro-2-quinolinyl)ethenyl)phenyl)-3-(2-(2-hydroxy-2-propyl)phenyl)thio) methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl) thio)-methyl) cyclopropane-acetic acid, pranlukast, zafirlukast, [2-[[2-(4-tert-butyl-2-thiazolyl)-5-benzofuranyl] oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts thereof and optionally in the form of the salts and derivatives thereof, the solvates and/or hydrates thereof.

EGFR-kinase inhibitors which may be used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl) amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl) amino]-6-{[4-(N,N-dimethylamino)-1-oxo-2-buten-1-yl] amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl) amino]-6-(4-hydroxy-phenyl)-7H-pyrrolo[2,3-d] pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl] amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl] amino}-quinazolone, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl) carbonyl]-piperidin-4-yloxy}-7-methoxy-quinazolione, 4-[(3-chloro-4-fluoro-phenyl)amino]-6-(piperidin-3-yloxy)-7-methoxy-quinazoline, 4-[(3-chloro-4-fluoro-phenyl) amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-

{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-ylethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the compounds may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Examples of antiallergics are: disodium cromoglycate, nedocromil.

Examples of ergot alkaloids are: dihydroergotamine, ergotamine.

Examples of substances suitable for inhalation include pharmaceutical compositions containing the above-mentioned active substances, and the salts and esters thereof and combinations of these active substances, salts and esters thereof.

The proportion of suspended drug in the finished preparation is between 0.001 and 5%, preferably 0.005 to 3%, particularly 0.01 to 2%. Surface-active substances are added in amounts of from 0.01 to 10%, preferably 0.05 to 5%, particularly 0.05 to 3% (%=percent by weight).

In the case of ipratropium bromide monohydrate the suspensions according to the invention preferably contain between 0.001 to 1%, particularly 0.005 to 0.5% ipratropium. Particularly preferred according to the invention are suspensions which contain 0.01 to 0.1% ipratropium.

In the case of salbutamol and the salts thereof the suspensions according to the invention preferably contain between 0.005 to 5%, particularly 0.025 to 2.5% salbutamol. Particularly preferred according to the invention are suspensions which contain 0.05 to 1% salbutamol.

In the case of tiotropium bromide monohydrate the suspensions according to the invention preferably contain between 0.001 to 1%, particularly 0.0012 to 0.8% tiotropium. Preferred according to the invention are suspensions which contain 0.002 to 0.5%, particularly preferably 0.008 to 0.4% tiotropium.

By all the active substances, e.g. tiotropium or ipratropium, is meant in each case the free ammonium cation. The propellant gas suspensions according to the invention are characterised in that they contain tiotropium or ipratropium in the form of the crystalline monohydrates. Accordingly, the present invention preferably relates to suspensions which contain crystalline tiotropium bromide monohydrate or ipratropium bromide monohydrate.

With regard to tiotropium bromide monohydrate suspensions which contain 0.001 to 0.62%, particularly preferably 0.002 to 0.5, most particularly preferably 0.002 to 0.06 of crystalline tiotropium bromide monohydrate are of particular interest.

The percentage amounts specified within the scope of the present invention are always percent by mass. If amounts by mass for tiotropium are expressed as percent by mass, the corresponding values for the crystalline tiotropium bromide monohydrate which is preferably used within the scope of the present invention may be obtained by multiplying by the conversion factor 1.2495. The same applies to ipratopium.

If anhydrous propellant gases are used, a small amount of water is added to them according to the invention. However, it is also possible according to the invention to use water-containing propellant gases, which should have a specific water content when used. This water which is added to or present in the finished suspension formulation is different from water which is chemically bound in one of the active substances or excipients. Within the scope of the present invention this non-chemically bound water is also referred to as free water, to distinguish it from the water which is molecularly or chemically bound to the active substance.

It has been found that the suspended particles of active substance change when the water content is too low. On the other hand it has been found that the particle sizes change if the water content is too high. The optimum water content may be determined individually for each substance. It has been found that the preferred amount of water in the propellant gas TG 227 ea or in mixtures of TG 227 ea with propellant gases selected from among propane, butane, pentane, dimethylether, $CHClF_2$, $CH_2F_2$, $CF_3CH_3$, isobutane, isopentane and neopentane, is generally 10 to 1000 ppm, particularly preferably 50 to 500 ppm, and most particularly preferably the amount of water is 100 to 450 ppm.

In the case of formulations containing ipratropium bromide monohydrate with propellant gas TG 227 ea the most preferred water content of the formulation is between 20 and 500 ppm, and the water content is particularly between 50 and 350 ppm.

In the case of tiotropium bromide monohydrate the preferred water content is comparable to that for ipratropium bromide monohydrate. The most preferred range is between 50 and 230 ppm.

It has also been found that the preferred quantity of water in the propellant gas TG 134 a or in mixtures of TG 134 a with propellant gases from the group propane, butane, pentane, dimethylether, $CHClF_2$, $CH_2F_2$, $CF_3CH_3$, isobutane, isopentane and neopentane is between 30 and 4000 ppm, particularly preferably between 150 and 2000 ppm and most particularly preferably between 350 and 1700 ppm.

In the case of formulations containing ipratropium monohydrate with propellant gas TG 134 a the most preferred water content of the formulation is between 70 and 1800 ppm, and in particular the water content is between 180 and 1300 ppm.

In the case of tiotropium monohydrate the preferred water content is similar to that for ipratropium bromide. The most preferred range is between 180 and 900 ppm.

If mixtures of the propellant gases TG 134 a and TG 227 ea are used, the preferred water contents are obtained from the mixing ratio of the two propellant gases.

According to the invention these amounts of water are added to the propellant gases or to the finished aerosol suspensions if the propellant gas, propellant gas mixture or the formulation does not contain any water (free water) in addition to the water chemically bound to the active substance. In the process, the water may have already been added to the propellant gas before the pharmaceutical suspension is prepared, or the pharmaceutical suspension may be prepared first with anhydrous propellant gas or propellant gas mixture and then the corresponding amount of water is added.

The amounts given in ppm are based on the liquefied propellant as the reference magnitude.

Within the scope of the present invention the term suspension formulation may be used instead of the term suspension. The two terms are to be regarded as equivalent within the scope of the present invention.

The propellant-containing inhalable aerosols or suspension formulations according to the invention may also contain other constituents such as surface-active agents (surfactants), adjuvants, antioxidants or flavourings.

The surface-active agents (surfactants) optionally present in the suspensions according to the invention are preferably selected from the group consisting of Polysorbate 20, Polysorbate 80, MYVACET® 9-45 (acetylated monoglyceride), MYVACET® 9-08 (acetylated monoglyceride), isopropyl myristate, oleic acid, propyleneglycol, polyethyleneglycol, BRIJ® (nonionic polyoxyethylene), ethyl oleate, glyceryl trioleate, glyceryl monolaurate, glyceryl monooleate, glyceryl monostearate, glyceryl monoricinoleate, cetylalcohol, sterylalcohol, cetylpyridinium chloride, block polymers, natural oil, ethanol and isopropanol. Of the above-mentioned suspension adjuvants Polysorbate 20, Polysorbate 80, MYVACET® 9-45 (acetylated monoglyceride), MYVACET® 9-08 (acetylated monoglyceride) or isopropyl myristate are preferably used. MYVACET® 9-45 (acetylated monoglyceride) or isopropyl myristate are most preferably used.

If the suspensions according to the invention contain surfactants these are preferably used in an amount of 0.0005-1%, particularly preferably 0.005-0.5%.

The adjuvants optionally contained in the suspensions according to the invention are preferably selected from the group consisting of alanine, albumin, ascorbic acid, aspartame, betaine, cysteine, phosphoric acid, nitric acid, hydrochloric acid, sulphuric acid and citric acid. Ascorbic acid, phosphoric acid, hydrochloric acid or citric acid are preferably used, while hydrochloric acid or citric acid is most preferably used.

If adjuvants are present in the suspensions according to the invention, these are preferably used in an amount of 0.0001-1.0%, preferably 0.0005-0.1%, particularly preferably 0.001-0.01%, while an amount of 0.001-0.005% is particularly important according to the invention.

The antioxidants optionally contained in the suspensions according to the invention are preferably selected from the group consisting of ascorbic acid, citric acid, sodium edetate, editic acid, tocopherols, butylhydroxytoluene, butylhydroxyanisol and ascorbylpalmitate, while tocopherols, butylhydroxytoluene, butylhydroxyanisol or ascorbylpalmitate are preferably used.

The flavourings optionally contained in the suspensions according to the invention are preferably selected from the group consisting of peppermint, saccharine, Dentomint®, aspartame and ethereal oils (for example cinnamon, aniseed, menthol, camphor), of which peppermint or Dentomint® are particularly preferred.

With a view to administration by inhalation it is essential to provide the active substances in finely divided form. For this purpose, the active substance is obtained in finely divided form either by grinding (micronising) or using other methods known in the prior art (e.g. precipitation, spray-drying). Methods of micronising active substances are known in the art. Preferably after micronising the active substance has a mean particle size of 0.5 to 10 µm, preferably 1 to 6 µm, particularly preferably 1.5 to 5 µm. Preferably at least 50%, preferably at least 60%, particularly preferably at least 70% of the particles of active substance have a particle size which is within the size ranges mentioned above. Particularly preferably at least 80%, most preferably at least 90% of the particles of active substance have a particle size which is within the size ranges mentioned above.

Surprisingly it has been found that suspensions may also be prepared which contain, in addition to the above-mentioned propellant gases, only the active substance or active substances and no other additives. Accordingly, in another aspect, the present invention relates to suspensions which contain only the active substance or active substances and no other additives.

The suspensions according to the invention may be prepared using methods known in the art. For this, the constituents of the formulation are mixed with the propellent gas or gases (optionally at low temperatures) and filled into suitable containers.

The above-mentioned propellant-containing suspensions according to the invention may be administered using inhalers known in the art (pMDIs=pressurized metered dose inhalers). Accordingly, in another aspect, the present invention relates to pharmaceutical compositions in the form of suspensions as hereinbefore described combined with one or more inhalers suitable for administering these suspensions. Moreover the present invention relates to inhalers, characterised in that they contain the propellant-containing suspensions according to the invention described hereinbefore.

The present invention also relates to containers (e.g. cartridges) which are fitted with a suitable valve adjusted before use with regard to the water content. The containers may be used in a suitable inhaler and contain one of the above-mentioned propellant-containing suspensions according to the invention. Suitable containers (e.g. cartridges) and processes for filling these cartridges with the propellant-containing suspensions according to the invention are known in the art.

In view of the pharmaceutical activity of anticholinergics the present invention also relates to the use of the suspensions according to the invention for preparing a pharmaceutical composition for inhalation or nasal administration, preferably for preparing a pharmaceutical composition for inhalative or nasal treatment of diseases in which anticholinergics may develop a therapeutic benefit.

Particularly preferably the present invention also relates to the use of the suspensions according to the invention for preparing a pharmaceutical composition for the inhalative treatment of respiratory complaints, preferably asthma or COPD, mucoviscidosis, cystic fibrosis; and also systemic complaints, such as pain, migraine, high blood pressure, erectile disorders.

The Examples that follow serve to illustrate the present invention in more detail, by way of example, without restricting it to their contents.

EXAMPLES OF FORMULATIONS

1.

| | |
|---|---|
| Ipratropium bromide monohydrate | 0.03 wt. % |
| Fenoterol hydrobromide | 0.07 wt. % |
| MYVACET ® type 9-08 (acetylated monoglyceride) | 0.4 wt. % |
| TG 227ea | 99.5 wt. % |
| Total | 100 wt. % (15.9 g) |

2.

| | |
|---|---|
| Ipratropium bromide monohydrate | 0.03 wt. % |
| Fenoterol hydrobromide | 0.07 wt. % |
| Isopropylmyristate | 0.4 wt. % |
| TG 227ea | 99.5 wt. % |
| Total | 100 wt. % (15.9 g) |

3.

| | |
|---|---|
| Ipratropium bromide monohydrate | 0.03 wt. % |
| Fenoterol hydrobromide | 0.07 wt. % |
| Tween 20 | 0.4 wt. % |
| TG 227ea | 99.5 wt. % |
| Total | 100 wt. % (15.9 g) |

4.

| | |
|---|---|
| Ipratropium bromide monohydrate | 0.03 wt. % |
| Fenoterol hydrobromide | 0.07 wt. % |
| Tween 80 | 0.4 wt. % |
| TG 227ea | 99.5 wt. % |
| Total | 100 wt. % (15.9 g) |

5.

| | |
|---|---|
| Ipratropium bromide monohydrate | 0.03 wt. % |
| Fenoterol hydrobromide | 0.07 wt. % |
| Isopropylmyristate | 10.00 wt. % |
| TG 227ea | 89.90 wt. % |
| Total | 100 wt. % (15.9 g) |

6.

| | |
|---|---|
| Ipratropium bromide monohydrate | 0.03 wt. % |
| Fenoterol hydrobromide | 0.07 wt. % |
| Isopropylmyristate | 10.00 wt. % |
| Soyalecithin | 0.004 wt. % |
| TG 227ea | 89.9 wt. % |
| Total | 100 wt. % (15.9 g) |

7.

| | |
|---|---|
| Ipratropium bromide monohydrate | 0.03 wt. % |
| Salbutamol sulphate | 0.19 wt. % |
| Tween 20 | 0.4 wt. % |
| TG 227ea | 99.38 wt. % |
| Total | 100 wt. % (15.9 g) |

8.

| | |
|---|---|
| Ipratropium bromide monohydrate | 0.03 wt. % |
| Salbutamol sulphate | 0.19 wt. % |
| TG 227ea | 99.78 wt. % |
| Total | 100 wt. % (15.9 g) |

Formulation examples 1 to 8 preferably contain between 50 and 300 ppm water.

9.

| | |
|---|---|
| Ipratropium bromide monohydrate | 0.04 wt. % |
| Salbutamol sulphate | 0.21 wt. % |
| TG 134a | 99.75 wt. % |
| Total | 100 wt. % (14.8 g) |

Formulation example 9 may contain between 200 and 1000 ppm water.

What is claimed is:

1. An aerosol suspension consisting of:
   particles of active substance with chemically bound water,
   at least 85 wt. % of a propellant gas TG 227 ea or TG 227 ea in admixture with at least one other propellant gas selected from among propane, butane, pentane, dimethylether, $CHClF_2$, $CH_2F_2$, $CF_3CH_3$, isobutane, isopentane and neopentane, wherein the aerosol suspension contains additional free water in addition to the water chemically bound to the active substance;

wherein said active substance is selected from ipratropium bromide monohydrate and tiotropium bromide monohydrate; and wherein the propellant gas TG 227 ea, or mixtures with this propellant gas, form a concentration of water between 50 and 230 ppm in the aerosol suspension.

2. The aerosol suspension according to claim 1, wherein it contains crystalline particles of active substance which bind the water as water of crystallization, hydrate or complex.

3. The aerosol suspension according to claim 1, wherein the amount of active substance is between 0.001 and 5%.

4. The aerosol suspension according to claim 1, wherein the amount of active substance is between 0.002 and 3%.

5. The aerosol suspension according to claim 1, wherein the amount of active substance is between 0.002 and 2%.

6. A method of treating a disease selected from the group consisting of asthma, COPD, mucoviscidosis and cystic fibrosis, comprising administering by inhalation or by nasal route a pharmaceutically effective amount of an aerosol suspension according to claim 1.

7. A method of treating a disease chosen from pain, migraine, hypertension and erectile disorder, comprising administering by inhalation or by nasal route a pharmaceutically effective amount of an aerosol suspension according to claim 1.

8. A process for preparing an aerosol suspension according to claim 1 comprising adding water to an anhydrous propellant gas or propellant gas mixture.

9. A container, wherein the container contains a propellant-containing aerosol suspension according to claim 1 and a suitable valve which is adjusted before use in relation to its water content.

* * * * *